United States Patent
McLean

[11] Patent Number: 5,969,255
[45] Date of Patent: *Oct. 19, 1999

[54] SYSTEM AND METHOD OF ULTRASONIC INSPECTION OF TUBULAR MEMBERS

[76] Inventor: Ted McLean, 3503 Cedar Knolls Dr., Suite A, Kingwood, Tex. 77399

[*] Notice: This patent is subject to a terminal disclaimer.

[21] Appl. No.: 08/924,841

[22] Filed: Sep. 5, 1997

Related U.S. Application Data

[63] Continuation-in-part of application No. 08/727,262, Oct. 8, 1996, Pat. No. 5,686,668.

[51] Int. Cl.$^6$ ....................................................... G01N 9/24
[52] U.S. Cl. .............................. 73/622; 73/637; 73/638; 73/639
[58] Field of Search ............................. 73/622, 636, 637, 73/638, 639, 640, 641, 635, 597, 598, 599, 600, 618

[56] References Cited

U.S. PATENT DOCUMENTS

| | | | |
|---|---|---|---|
| 4,041,773 | 8/1977 | Hauldren | 73/622 |
| 4,108,004 | 8/1978 | Murakami | 73/638 |
| 4,213,345 | 7/1980 | Dufour | 73/637 |
| 4,312,230 | 1/1982 | Bricher | 73/638 |
| 4,893,512 | 1/1990 | Tanimoto | 73/622 |
| 4,995,320 | 2/1991 | Sato et al. | 73/638 |
| 5,549,004 | 8/1996 | Nugent | 73/622 |

FOREIGN PATENT DOCUMENTS

| | | | |
|---|---|---|---|
| 2105466 | 3/1983 | United Kingdom | 73/622 |

*Primary Examiner*—Hezron Williams
*Assistant Examiner*—Thuy Vinh Tran
*Attorney, Agent, or Firm*—Harrison & Egbert

[57] ABSTRACT

A system for ultrasonic inspection of a tubular member using an ultrasonic inspection unit having a platform, a guide member with a longitudinal axis, a wheel connected to the platform and contacting a surface of the tubular member for moving the platform along and around the tubular member relative to a rotation of the tubular member, and a bearing support connected to the platform at a location spaced from the wheel. The bearing support contacts the guide member for supporting the platform on the guide member and allowing the platform to move longitudinally in a direction along the longitudinal axis of the guide member in response to the moving of the guide wheel. A tubular member rotation mechanism receives the tubular member and rotates the tubular member around a longitudinal axis of the tubular member.

18 Claims, 8 Drawing Sheets

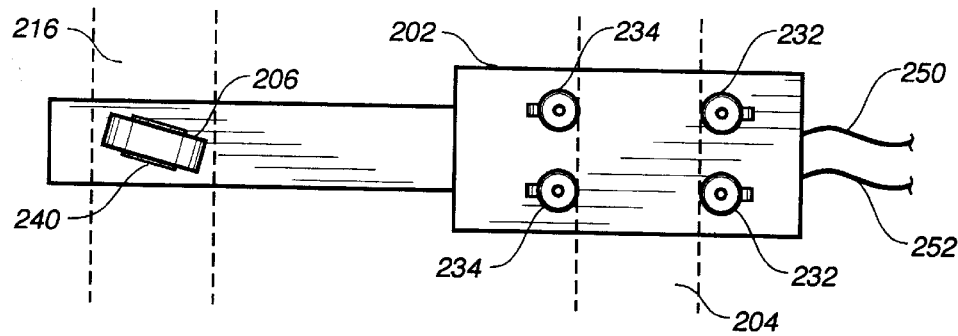
FIG. 10
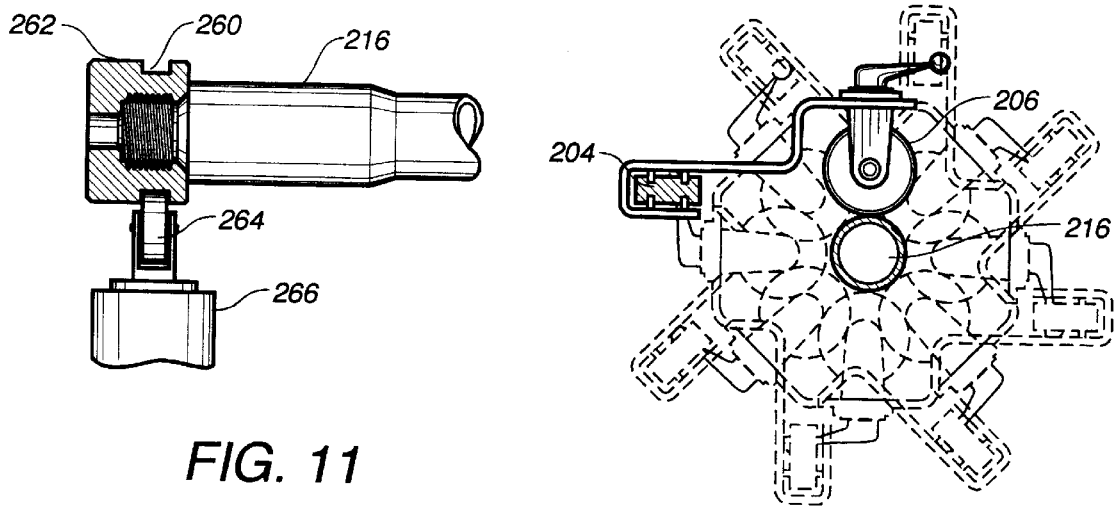
FIG. 11
FIG. 12
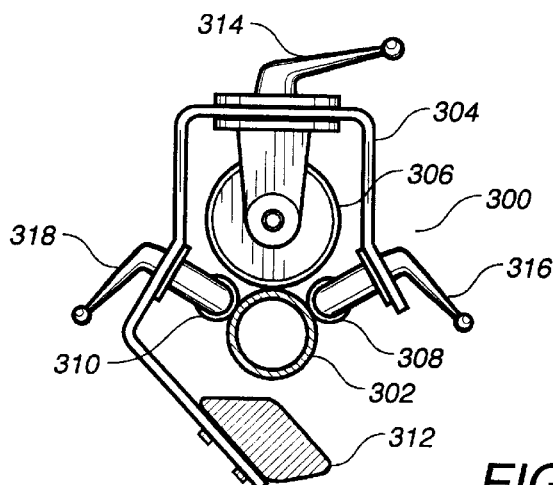
FIG. 13

SYSTEM AND METHOD OF ULTRASONIC INSPECTION OF TUBULAR MEMBERS

RELATED APPLICATIONS

The present application is a continuation-in-part of U.S. patent application Ser. No. 08/727,262, filed on Oct. 8, 1996, now U.S. Pat. No. 5,686,668 and entitled "SYSTEM AND METHOD OF ULTRASONIC INSPECTION OF TUBULAR MEMBERS".

TECHNICAL FIELD

The present invention relates to the ultrasonic inspection of tubular members. More particularly, the present invention relates to apparatus and methods for non-destructively inspecting an entire length of a tubular member. Furthermore, the present invention relates to systems whereby the existing tubular member supports an ultrasonic inspection unit.

BACKGROUND ART

Drill pipe is used for the drilling of oil and gas wells. Typically, a large number of drill pipes extend from the surface of the earth down to the drilling bit. When each of the drill pipes is connected in end-to-end relationship, the "drill string" is formed.

During the drilling of oil wells, it is very important that each of the drill pipes has proper integrity and strength. As a result, an ultrasonic inspection of each of the drill pipes is necessary and important. Conventionally, ultrasonic inspection is carried out so as to determine whether or not any minute cracks or deformations exist in the drill pipe. If cracks and/or deformations are found in the drill pipe, then the drill pipe should not be used. Ultrasonic inspection involves transmitting an ultrasonic wave through the drill pipe and receiving the reflected signal of the ultrasonic beam. Various diagnostic programs and devices are used so as to properly analyze the results of the ultrasonic inspection.

At present, hand-held ultrasonic units are used manually by an operator to inspect the ends of the drill pipe. This area is known as the critical end area because this area is where most of the failures occur. Since the distance to be inspected at the end of the drill pipe is short, the ultrasonic beam is narrow. The ultrasonic inspection unit travels slowly and is held by the operator. There are various ultrasonic inspection units that carry out complete inspection of drill pipe. However, these units are large trailer mounted units or fixed units which are not easily transportable. These inspection units are mostly installed in pipe mills or large pipe yards. Typically, the pipe is delivered to the inspection unit. These units function by running the pipe on conveyors through one end of the inspection unit, under the inspection sensors, and out the other side.

It is an object of the present invention to provide a method and apparatus for the inspection of tubular members.

It is another object of the present invention to provide a method and apparatus for the inspection of tubular members which serves to inspect the entire length of the tubular member.

It is a further object of the present invention to provide a method and apparatus for the inspection of tubular members which allows for on-site inspection of the tubular member.

It is a further object of the present invention to provide a method and apparatus for the inspection of tubular members which allows the tubular member being inspected to act as a bridge on which an inspection cart runs the entire length of the tubular member.

It is a further object of the present invention to provide a method and apparatus for the inspection of tubular members which is easy to use, relatively inexpensive, and labor efficient.

These and other objects and advantages of the present invention will become apparent from a reading of the attached specification and appended claims.

SUMMARY OF THE INVENTION

The present invention is a system for the ultrasonic inspection of a tubular member using an ultrasonic inspection unit. This system comprises a platform, a guide member having a longitudinal axis, a wheel means connected to the platform and contacting a surface of the tubular member for moving the platform along and around the tubular member relative to a rotation of the tubular member, and a bearing means connected to the platform at a location spaced from the wheel means. The bearing means contacts the guide member for supporting the platform on the guide member and for allowing the platform to move longitudinally in a direction along the longitudinal axis of the guide member in response to the moving of the wheel means. A tubular member rotation device is disposed proximate the tubular member for receiving the tubular member and for rotating the tubular member around a longitudinal axis of the tubular member.

The guide member is disposed in a spaced and generally parallel relationship to the tubular member. In the preferred embodiment of the present invention, the tubular member is a first drill pipe and the guide member is a second drill pipe. A pipe rack is positioned below the first and second drill pipes so as to support the drill pipes above the earth.

The wheel means includes a non-destruction inspection device which is electrically connected to the inspection unit for ultrasonically inspecting the tubular member. The wheel is rotatably mounted on the platform so as to have a surface contacting the surface of the tubular member. The wheel has an axis about which the wheel rotates. This axis is angularly offset from the longitudinal axis of the tubular member.

The guide member is a longitudinal member arranged in spaced parallel relationship to the tubular member. A guide member support mechanism is connected to the guide member for positioning the guide member at a desired level relative to the tubular member.

In the present invention, the bearing means includes a plurality of roller members that are rotatably mounted to the platform. Each of the roller members has an axis about which the roller member rotates. This axis is transverse to the longitudinal axis of the guide member. Specifically, the roller members include a first pair of roller members in surface-to-surface contact with the guide member on one side of the guide member. A second pair of roller members is in surface-to-surface contact with the guide member on another side of the guide member.

In an alternative embodiment of the present invention, the guide member is actually the tubular member. In this embodiment, the bearing means is radially spaced from the wheel means relative to the guide member. Specifically, a first roller member is in surface-to-surface contact with the guide member on one side of the wheel, and a second roller member is in surface-to-surface contact with the guide member on an opposite side of the wheel. A counterbalance is connected to the platform for supporting the wheel at a desired position on the tubular member as the tubular member rotates.

BRIEF DESCRIPTION OF THE DRAWINGS

FIG. 10 is a bottom view of the ultrasonic inspection cart as used in the alternative embodiment of FIG. 8.

FIG. 11 is a detailed view of circled area A of FIG. 8.

FIG. 12 is a diagrammatic illustration of the system of the alternative embodiment of FIG. 8 showing the positioning of the guide member relative to the inspected drill pipe.

FIG. 13 is an end view of a second alternative embodiment of the present invention.

DETAILED DESCRIPTION OF THE INVENTION

Figure 1:
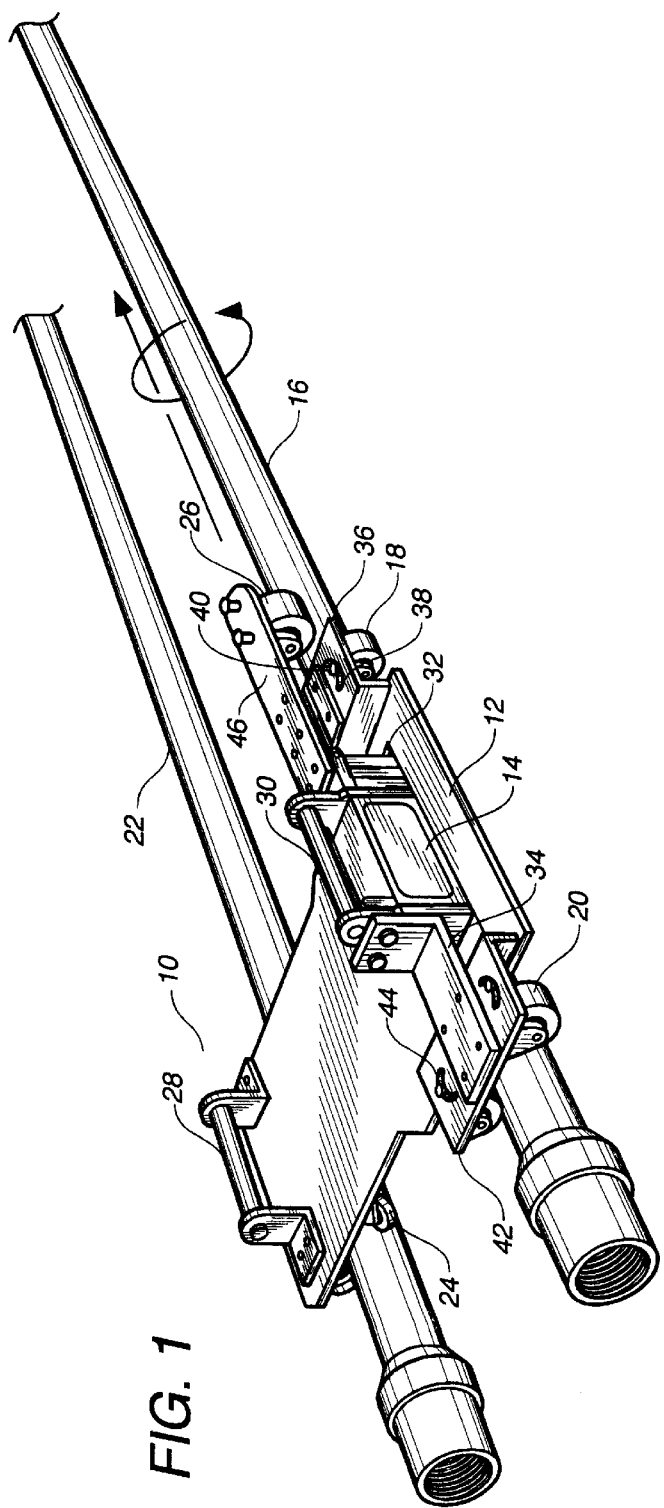
FIG. 1 is a perspective view of the inspection cart of the present invention as applied onto a pair of tubular members.

Referring to FIG. 1, there is shown at 10 the system of the present invention for the inspection of tubular members, in particular, drill pipe. The system 10 of the present invention includes a platform 12 having a non-destructive inspection unit 14 placed thereon. The cart 12 is supported upon a first tubular member 16 through the use of a first pair of wheels 18 and a second pair of wheels 20. The opposite side of the platform 12 is supported on the second tubular member 22 by a bearing arrangement 24. A sensor wheel 26 extends outwardly from the platform 12 so that the wheel 26 contacts a surface of the first tubular member 16. In the present application, certain terms are employed for purposes of simplicity. As used herein, the term "platform" can refer to flat surfaces, connector members or other structures that connect the wheels 18 and 20 and also support the inspection unit 14. Also, as used herein, the term "tubular member" can include drill pipe, casings, tubes, and solid bar stock having a circular cross-section. Furthermore, the term "bearing arrangement" can include ball bearings, small wheels, or other rotatable items that can ride on a surface of the tubular member.

In FIG. 1, it can be seen that the platform 12 is a generally flat platform 12 that has a handle 28 extending upwardly from a top surface of the platform 12 generally adjacent to the second tubular member 22 and above the bearings 24. A second handle 30 is affixed above the inspection unit 12 on the side of the platform 12 in alignment with the first pair of wheels 18 and the second pair of wheels 20. The platform 12 includes a receiving area 32 formed therein so as to be positioned between the first pair of wheels 18 and the second pair of wheels 20. The receiving area 32 serves to receive the inspection unit 14 therein and to allow the inspection unit to be directly supported on a surface of the tubular member 16. The platform 12 is configured so as to move in close proximity to a top surface of the tubular members 16 and 22.

The inspection unit 14 is a non-destructive inspection unit. Various types of non-destructive inspection units can be employed in the present invention. For example, the platform 12 could receive ultrasonic inspection devices, electromagnetic inspection devices, hall effect inspection units and, possibly, magnetic resonance imaging units. However, the preferred embodiment of the present invention contemplates ultrasonic inspection units. These ultrasonic inspection units serve to transmit an ultrasonic wave through a liquid medium and through the wall of the tubular member 16 so that the reflection of the ultrasonic wave will be indicative of flaws or deformations in the material of the tubular member 16. Normally, the inspection unit 14 is used as a hand held unit for the inspection of the ends of the drill pipe, as described herein previously in the "Background Art". Suitable bracketing 34 is provided so as to secure the ultrasonic inspection unit 14 within the receiving area 32 of the platform 12. The inspection unit has small wheels which support the inspection unit on the tubular member. The ultrasonic signal is transmitted by the sensor wheel 26.

The first pair of wheels 18 are positioned at one end of the platform 12. The first pair of wheels 18 has an axis of rotation which is canted at an angle relative to the longitudinal axis of the tubular member 16. A more detailed illustration of such canting is provided in FIG. 4. Similarly, the second pair of wheels 20 is positioned at an end of the platform 12 opposite the first pair of wheels 18. The second pair of wheels 20 is also canted at the same angle as the first pair of wheels 18 with respect to the longitudinal axis of the tubular member 16. Importantly, it can be seen that the first pair of wheels 18 is supported by a L-shaped member 36 which extends outwardly of the platform 12. The L-shaped member 36 includes an arcuate slot 38 formed therein. The wheels 18 include a guide member 40 which extends into the arcuate slot 38. The guide member 40 is suitable for fixing in a position along the arcuate slot 38 so as to fix a cant of the first pair of wheels 18 relative to the longitudinal axis of the tubular member 16. A similar L-shaped bracket 42 is provided so as to support the second pair of wheels 20 in a position relative to the tubular member 16. The L-shaped bracket 42 also includes arcuate slots 44 which receive a guide member from the second pair of wheels 20. The guide member in the arcuate slot is suitable for fixing the cant of the second pair of wheels 20 at a same angle as the cant of the first pair of wheels 18.

In FIG. 1, it can be seen that the sensor wheels 26 extend outwardly from the platform 12 by an arm 46. Arm 46 is positioned in a location adjacent to the inspection unit 14 and the handle 30. The area 46 is flexible so as to be able to ride up the end of upset pipe. The sensor wheel 26 serves to rotate during the movement of the platform 12 along the tubular member 16. The sensor wheel 26 is connected to the inspection unit 14 by suitable electronics so as to transmit an ultrasonic signal into the tubular member 14. The sensor wheel 26 can be canted at the same angle as the wheels 18. A suitable slot can be provided in the area 46 to accommodate the angular adjustment of the sensor wheel 26.

Figure 2:
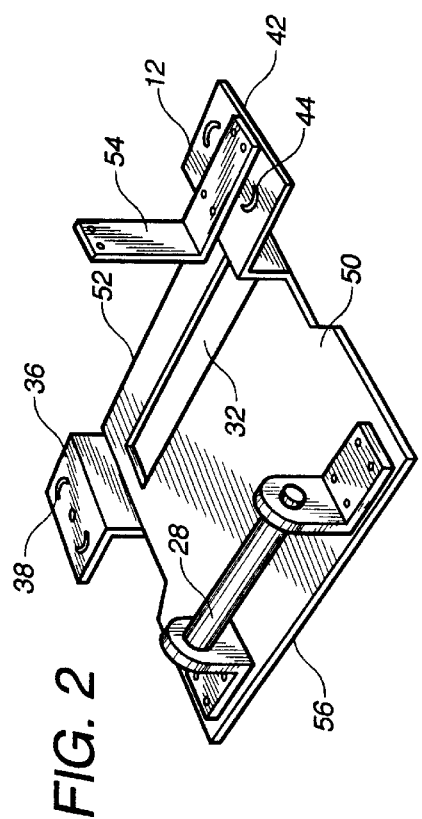
FIG. 2 is a perspective view of the platform of the cart of the present invention.

FIG. 2 is an isolated view of the platform 12. Initially, it can be seen that the platform 12 includes a flat surface 50. The flat surface 50 will extend between the first tubular member 16 and the second tubular member 22. The rectangular receiving area 32 is illustrated as in a location adjacent to side 52 of the platform 12. A first L-shaped bracket 36 extends upwardly and outwardly from one end of the flat surface 50. The L-shaped bracket 36 includes arcuate slots 38 for the receiving of the guide members from the first pair of wheels. A second L-shaped bracket 42 extends outwardly from an opposite end of the flat surface 50. The second L-shaped bracket 42 also includes arcuate slots 44 for receiving the guide members of the second pair of wheels 20. An L-shaped member 54 is affixed to the top surface of the second L-shaped bracket 42. The L-shaped member 54 is suitable for the attachment of handle 30 and for the receiving of the inspection unit 14 within the receiving area 32. The handle 28 is affixed to the flat surface 50 and extends upwardly therefrom. The handle 28 is positioned adjacent to the side 56 of the surface 50.

Figure 3:
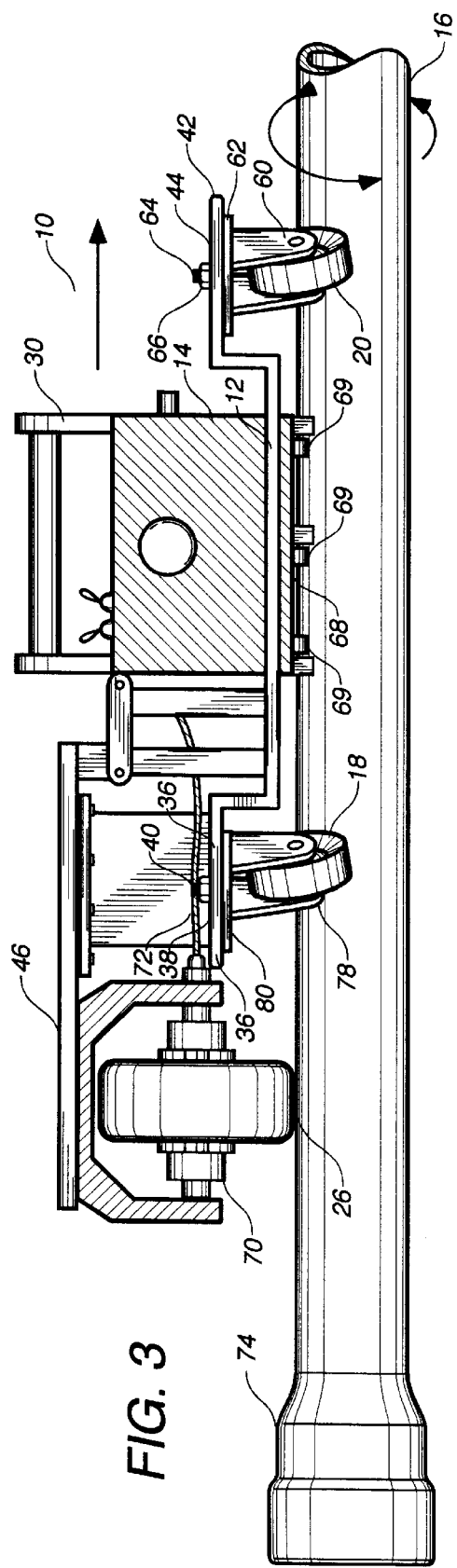
FIG. 3 is a side elevational view of the inspection cart as placed upon a tubular member.

FIG. 3 shows the configuration of the cart 10 positioned on the first tubular member 16. Initially, it can be seen that the second pair of wheels 20 are rotatably supported within a caster 60. The caster 60 is affixed to a bar 62. A guide member 64 extends upwardly from the bar 62 and outwardly of the L-shaped bracket 42 through the arcuate slot 44. As can be seen, the guide member 64 is a threaded member which includes a nut 66 for securing the guide member 64 in a proper position within the arcuate slot 44. By the loosening of the nut 66, the angle of cant of the second pair of wheels 20 can be suitably adjusted. By changing the angle of cant, the rate of movement of the cart 10 relative to the tubular member 16 can be varied.

The L-shaped bracket 42 extends outwardly from the platform 12. The inspection unit 14 is supported on the top surface of the platform 12. It can be seen that the inspection unit 14 includes a bottom surface 68 which is positioned in very close proximity to the exterior surface of the tubular member 16. Small wheels 69 on the bottom of the inspection unit 14 allow the inspection unit to be supported on the tubular member 16. The handle 30 extends upwardly from the top surface of the inspection unit 14.

An arm 46 extends outwardly from the inspection unit 14 and from the platform 12. Arm 46 serves to support the sensor wheel 26 in a location forward of the first pair of wheels 18. The sensor wheel 26 is rotatably mounted within frame 70 so as to allow the wheel 26 to rotate as the cart 14 traverses the length of the tubular member 16. An electrical line 72 extends from the axis of rotation of the wheel 26 so as to provide sensing information to the inspection unit 14. The sensor wheel 26 operates in a similar fashion as sensor wheels of conventional hand-held inspection units. A suitable means of data transfer can be connected to the inspection unit 14 so as to allow the ultrasonic inspection data to be transmitted to an instrument package exterior of the tubular member rack. Additionally, a liquid hose can be connected to the sensor wheel 26 so that the liquid medium can be applied to the surface of the tubular member.

It can be seen in FIG. 3 that the first pair of wheels 18 are canted at an angle relative to the longitudinal axis of the tubular member 16. The first pair of wheels 18 are received within casters 78 so as to allow the wheels 18 to rotate freely therein. The casters 78 are mounted on a bar 80. The guide member 40 extends upwardly through the arcuate slot 38 on the L-shaped bracket 36. The guide member 40 is fixed in a position within the arcuate slot 38 by the use of a nut.

Figure 4:
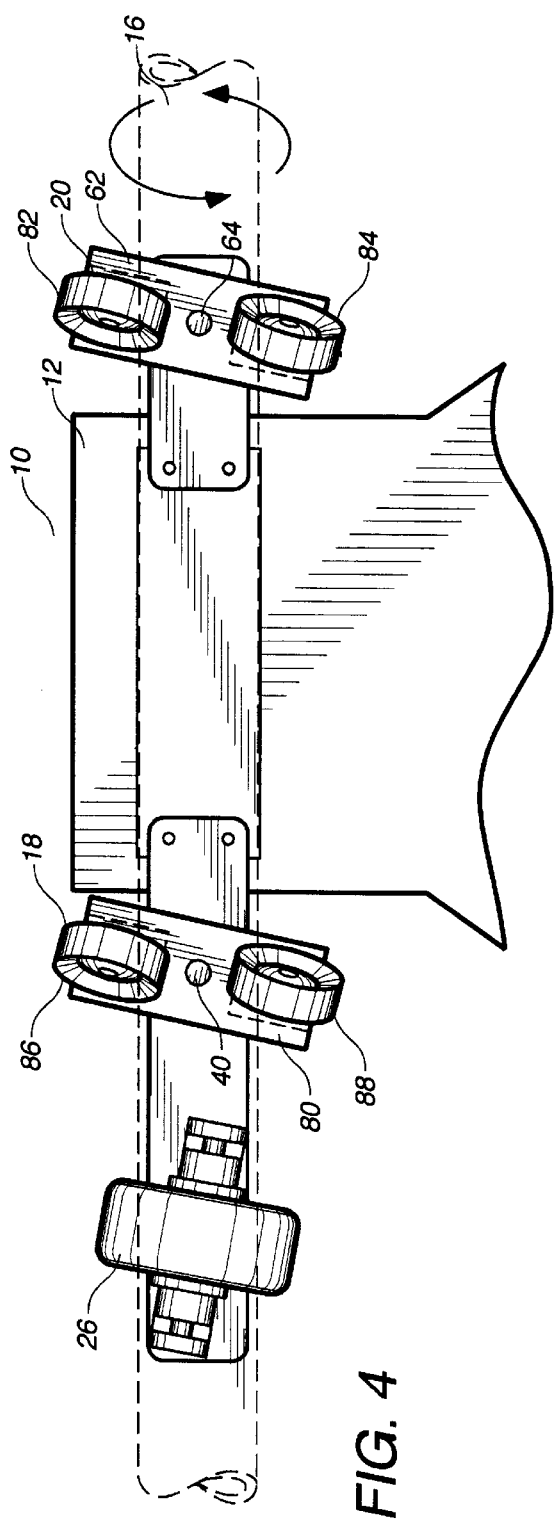
FIG. 4 is a bottom view of the inspection cart of the present invention with the tubular member shown in transparent fashion.

In FIG. 4, the tubular member 16 is illustrated in transparent fashion so that the actual canting of the first pair of wheels 18 and the second pair of wheels 20 can be properly seen. Initially, it can be seen that the second pair of wheels 20 includes a first wheel 82 and a second wheel 84 which are mounted on bar 62. The guide member 64 is mounted in the center of the bar 62 so as to allow a desired amount of pivotal movement so that the wheels 82 and 84 can be properly canted. Similarly, the first pair of wheels 18 includes a first wheel 86 and a second wheel 88. Wheels 86 and 88 are supported on bar 80. The guide member 40 is formed centrally of the bar 80 so as to allow a proper pivoting of the first pair of wheels 18. Ideally, the first pair of wheels 18 and the second pair of wheels 20 should have a similar cant so that the wheels will cause the platform 12 of the cart 10 to move along the length of the tubular member 16 when the tubular member 16 is rotated. If the wheels 18 and 20 were not canted, then the platform 12 of the cart 10 would remain in a stationary position on the tubular member 16.

It can be seen in FIG. 4 that the sensor wheel 26 is also canted at an angle similar to the angle of the first pair of wheels 18 and the second pair of wheels 20. As such, the sensor wheel 26 will not resist the movement of the cart 10 during the traversing of the tubular member 16. The sensor wheel 26, wheels 86 and 88 of the first pair of wheels 18, and wheels 82 and 84 of the second pair of wheels 20 will all contact a surface of the tubular member 16.

Figure 5:
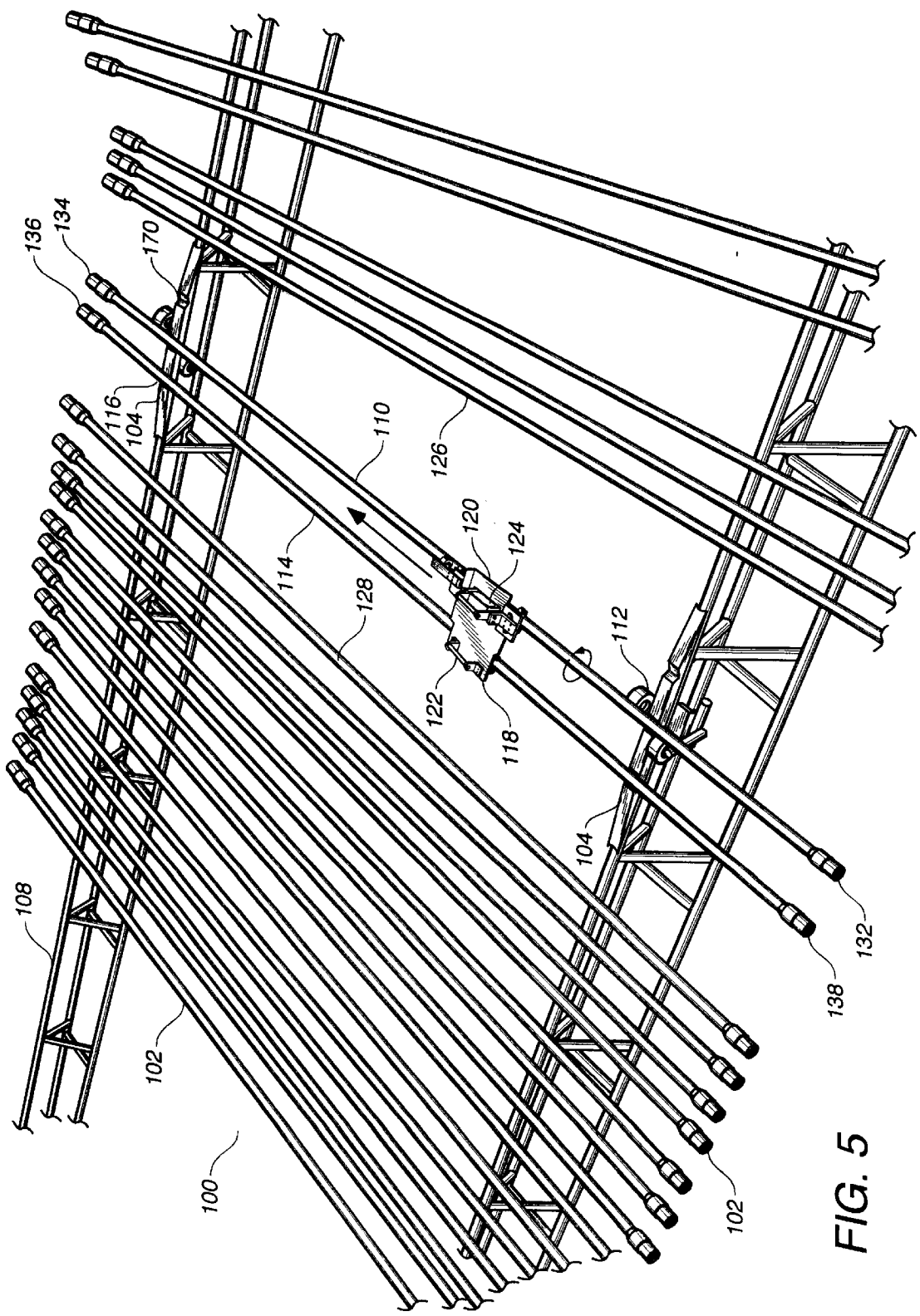
FIG. 5 is a perspective view of the method of the system of the present invention showing, in particular, the method of inspecting tubular member.

FIG. 5 is illustrative of the method 100 of the present invention for the non-destructive inspection of tubular members. Initially, in FIG. 5, it can be seen that the tubular members 102 are supported on the top surface of a tubular member support rack 104. The tubular member support rack 104 is mounted onto the top surface of a first rail 106 and a second rail 108. The rails 106 and 108 are positioned in parallel alignment. Each of the tubular members 102 are supported on the rails 106 and 108.

Initially, in FIG. 5, it can be seen that a tubular member 110 is received within a drive roller 112 on the tubular member support rack 104. The drive roller 112 serves to impart rotational movement to the tubular member 110. A second tubular member 114 is positioned in generally parallel relationship to the tubular member 110 on the tubular member support rack 104. A notch 116 can be formed in the support rack 104 so that the second tubular member 114 can be placed a desired distance from the first tubular member 110.

Importantly, it can be seen that the cart 118 is placed onto the top surface of the tubular members 110 and 114. The pairs of wheels on one side 120 of the cart 118 contact the surface of the first tubular member 110. The bearings on the other side 122 of the cart 118 are positioned onto a surface of the second tubular member 114. The inspection unit 124 is positioned on the top surface of the cart 118 so as to allow for the ultrasonic inspection of first tubular member 110.

In the method of the present invention, the first tubular member 110 is initially rolled along the rails 106 and 108 until the tubular member 110 is positioned into the drive roller 112 on the support rack 104. Next, the second tubular member 114 is rolled along the rails 106 and 108 until it is placed into the notch 116 on the support rack 104 so as to be in a proper position in parallel relationship to the first tubular member 110.

The inspection cart 108 is then placed onto the first tubular member 110 and onto the second tubular member 114 such that the wheels of the inspection cart 118 contact a surface of the first tubular member 110 and the bearings of the cart 118 contact the surface of the second tubular member 114. The first tubular member 110 is rotated by the drive roller 112 such that the inspection cart 118 moves longitudinally along the first tubular member 110 and the second tubular member 114. While the cart 118 traverses the length of the tubular members 110 and 114, the ultrasonic inspection unit 124 transmits and receives inspection data relative to the structure of the tubular member 110.

After the inspection cart 118 has transversed the desired length of the tubular members 110 and 114, the handles of the inspection cart 118 are grabbed so that the inspection cart 118 can be lifted from the tubular members 110 and 114. After the inspection cart 118 is removed, the first tubular member 110 is removed from the drive roller 120 and will move to an opposite side of the drive roller (as shown by tubular member 126 in FIG. 5). The second tubular member 114 is then moved from its position in notch 116 into the drive roller 112. A third tubular member 128 is then rolled into generally parallel relationship to the second tubular member 114 and is positioned in the notch 116. The inspection cart 118 can then be placed onto the second tubular member 114 and the third tubular member 128 such that the wheels of the inspection cart 118 contact a surface of the second tubular member 114 and the bearings of the inspection cart 118 contact the surface of the third tubular member 128. The second tubular member 114 is then rotated such that the inspection cart moves longitudinally along the second tubular member 114 and the third tubular member 128. Ultrasonic inspection data is transmitted from and received by the inspection unit 124 as the inspection cart 118 moves along the second tubular member 114. After this procedure is completed and the cart 118 traverses the length of the second tubular member 114, the second tubular member 114 can be removed from the drive roller 112 and moved to the other side of the drive roller. The process can continue for all of the tubular members 102 on the tubular member support rack 104.

In the present invention, it is possible to avoid the necessity of bringing the inspection cart 118 back to the same starting point on each of the tubular members which are tested. In particular, it is possible to place the inspection cart 118 at the opposite end of the tubular member from that where the inspections started on the previous tubular member. This can be accomplished by changing the direction of rotation of the drive roller 112 such that the second tubular member 114 rotates in an opposite direction than did the first tubular member 110. In other words, the inspection unit 118 initially moves from end 132 of the first tubular member 110 to the opposite end 134 of the first tubular member 110. When the inspection cart 118 is placed onto the second tubular member 114 and the third tubular member 128, the inspection cart 118 will move from the end 136 of the second tubular member 114 to the end 138 of the second tubular member 114. As such, the present invention enhances the efficiency of the inspection process. Furthermore, within the concept of the present invention, another notch can be formed in the support rack 104 so that tubular members on the opposite side of the drive roller 112 can be positioned properly for inspection.

Figure 6:
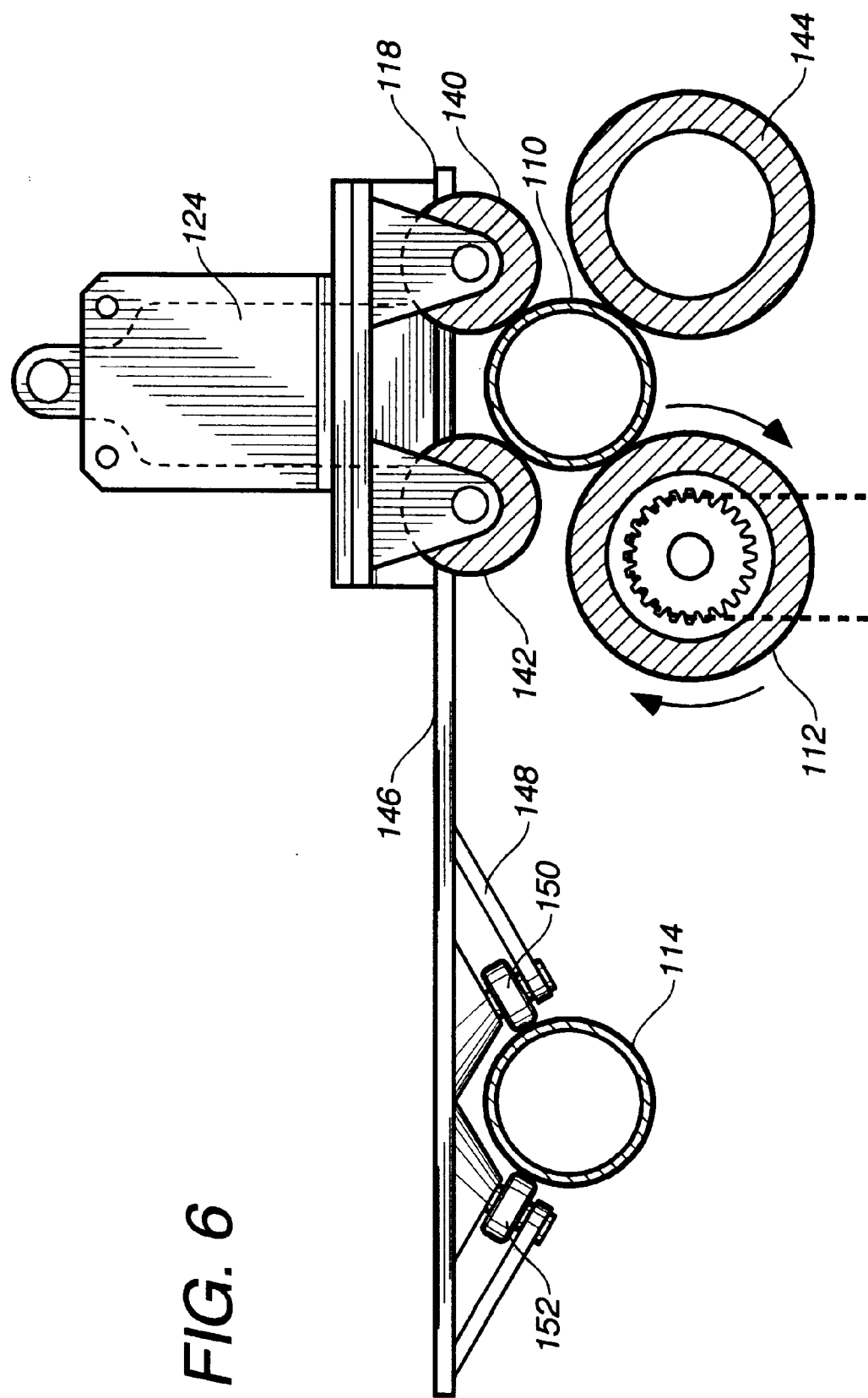
FIG. 6 is a cross-sectional side view of the inspection cart as placed on the rotatable tubular member in accordance with the method of the present invention.

FIG. 6 shows a detailed view of the operation of the drive roller 112 relative to the movement of the inspection cart 118. Initially, in FIG. 6, it can be seen that the wheels 140 and 142 contact the surface of the tubular member 110. The drive roller 112 is a chain driven drive roller such that a motor is provided which will rotate the drive roller 112 in a desired direction. As the roller 112 rotates, it will rotate the tubular member 110 in an opposite direction. The tubular member 110 is supported on its opposite side by a free roller 144. The counterclockwise rotation of the tubular member 110 will cause each of the wheels 140 and 142 to rotate in a clockwise direction. Since the wheels 140 and 142 are canted such that their axes of rotation are canted at an angle relative to the longitudinal axis of the tubular member 110, the cart 118 and associated inspection unit 124 will move longitudinally along the length of the tubular member 110.

In FIG. 6, it can be seen that the cart 118 has platform 146 formed thereon. At the opposite end of the platform 146 from the wheels 140 and 142 is a bearing arrangement 148. The bearing arrangement 148 includes a first roller 150 and a second roller 152 for supporting the platform 146 a desired distance above the tubular member 114. The first roller 150 has an axis of rotation which is transverse to the longitudinal axis of the tubular member 114. Similarly, the second roller 154 has an axis or rotation which is transverse to the longitudinal axis of the tubular member 114. Each of the rollers 150 and 152 are free rollers which allow the platform 146 to move linearly along the length of the tubular member 114. Each of the rollers 150 and 152 will rotate during the movement of the platform 146 along the tubular members 110 and 114. Since the rollers 150 and 152 are not driven, the rollers 150 and 152 serve to support the platform 146 and to allow the platform 146 to roll along the length of the second tubular member 114.

Figure 7:
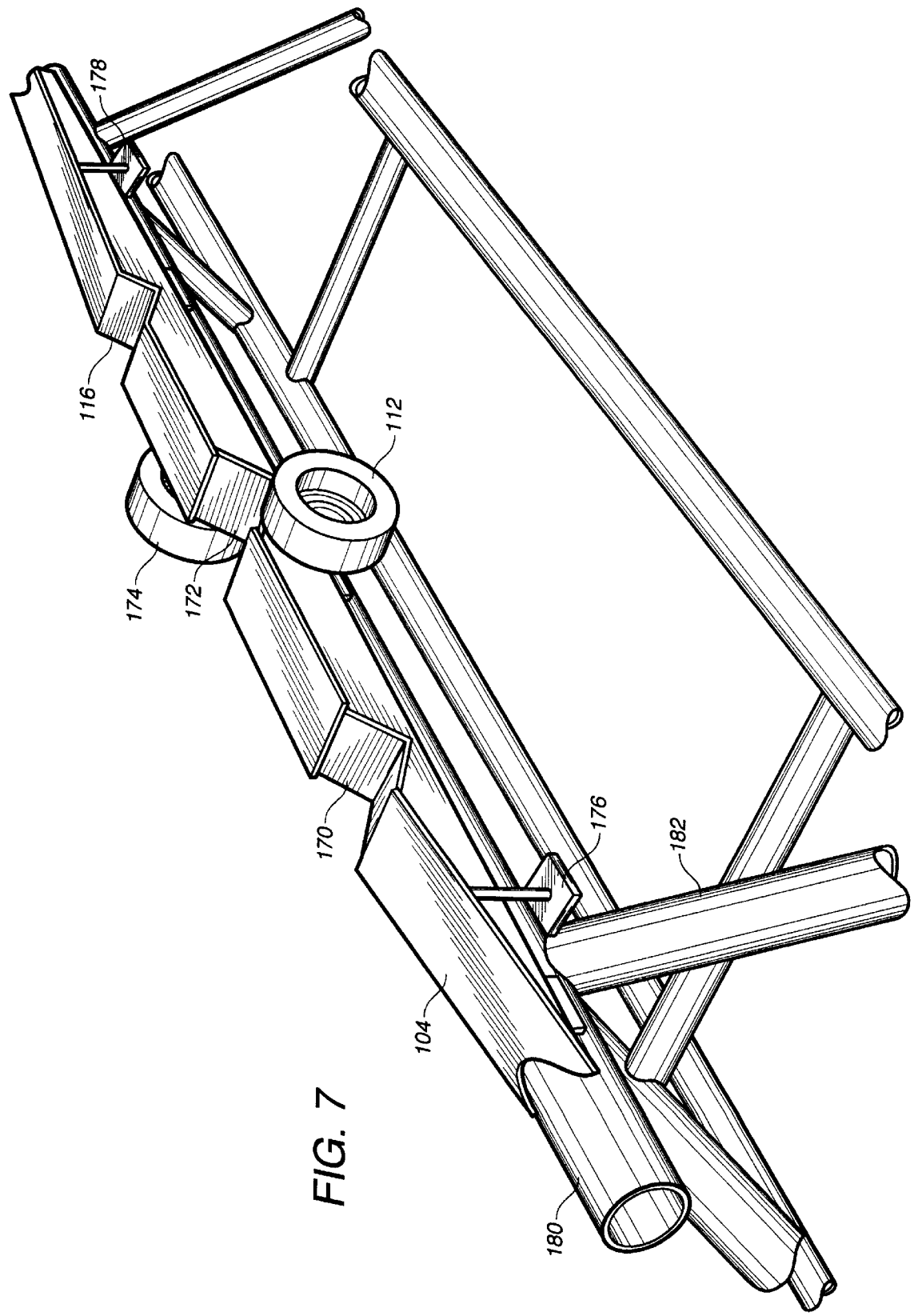
FIG. 7 is a perspective view showing the drive rollers and tubular member support rack as attached to a tubular member stand.

Referring to FIG. 7, the structure of the tubular member support rack 104 is illustrated with particularity. As can be seen, the tubular member support rack 104 includes notch 116 and notch 170 on opposite sides of the drive roller 102. Each of the notches 116 and 170 serves to allow a tubular member to be positioned in generally parallel and properly spaced relationship from the tubular member residing in notch 172. The tubular member which is received within notch 172 is the "driven" tubular member. Rotation to the tubular member is imparted by way of the drive roller 112 and the drive roller 174. Any rotational movement imparted by either of the drive rollers 112 and 174 to the tubular member received within the notch 172 will cause the tubular member to rotate, as described herein previously.

Importantly, it can be seen that the tubular member support rack 104 is mounted by clamps 176 and 178 onto the top surface 180 of the tubular member stand 182. As such, the configuration of the present invention can be applied onto conventional tubular member stands. It is simply necessary to loosen the clamps 176 and 178 such that the tubular member support rack 104 can be installed onto a top surface of a tubular member stand 182. A corresponding support rack can be applied to the opposite rail of the tubular member stand. The opposite tubular member support rack will have a similar configuration as that shown in FIG. 7, but for the drive rollers 112 and 174.

In the present invention, the tubular member which is actually being inspected serves as a "bridge" for moving the inspection unit along the entire length of the tubular member. The present invention allows the same material which is inspected to act as a bridge on which the inspection cart runs the entire length of the tubular member. As such, it is not necessary to have expensive equipment available which must be used for the inspection of tubular members. Furthermore, the present invention allows the hand-held inspection units (which are currently used for the inspection of the ends of the pipe) to be used effectively for the entire length of the tubular member.

Figure 8:
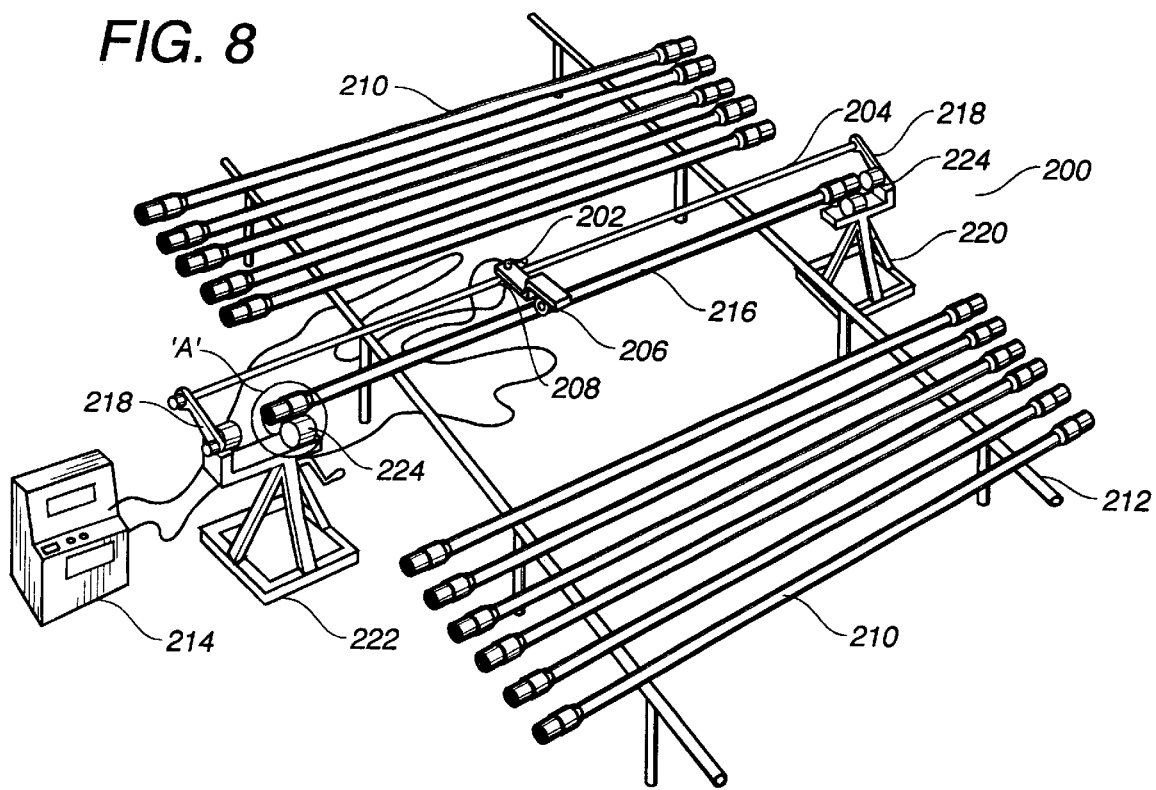
FIG. 8 shows the system of ultrasonic inspection in accordance with an alternative embodiment of the present invention.

Referring to FIG. 8, there is shown at 200 an alternative embodiment of the system for ultrasonic inspection of a tubular member. The system 200 includes a platform 202, a guide member 204, a wheel 206, and a bearing arrangement 208. In the system 200, it can be seen that there are a plurality of drill pipes 210 that are supported on a drill pipe rack 212 a desired distance above the earth. An ultrasonic inspection unit 214 is connected by electrical lines to the ultrasonic inspection wheel 206 on the platform 202. As such, ultrasonic signals can be transmitted and received from the ultrasonic inspection unit from the platform 202.

Unlike the previous embodiment, the system 200 includes a guide member 204 which is disposed in spaced and generally parallel relationship to tubular member 216. Tubular member 216 is the drill pipe which is the subject of the ultrasonic inspection. The guide member 204 is connected to a guide member support mechanism 218 which extends outwardly from the supports 220 and 222 of the tubular member 216. The guide member support mechanism 218 is connected to the guide member 204 so as to position the guide member 204 at a desired angle relative to the tubular member and at a desired elevation above or below the pipe rack 212 or at a desired level above the earth. The supports 220 and 222 are air jacks which serve to lift the drill pipe a desired distance above the pipe rack 212 during the inspection process. The air jacks lower the drill pipe following the inspection. The drill pipe can then be rolled from the supports 220 and 222.

As used in the alternative embodiment of the system 200, the guide member 204 can be a tubular member, a section of drill pipe, a solid rod, a square rod, or other longitudinal member. Since the guide member support mechanism 218 serves to lift the guide member 204 relative to the pipe rack 202 and to position the guide member 204 at a desired angle relative to the longitudinal axis of the tubular member 216, the guide member 204 can be positioned as desired. When the guide member 204 is lifted, then tubular members on one side of the rack 212 can be moved so as to be received by the tubular member support members 220 and 222.

In the system 200, the bearings 208 are connected to the platform 202 at a location spaced from the wheel 206. The bearings 208 contact the guide member 204 so as to support the platform 202 on the guide member 204 and to allow the platform 202 to move longitudinally in a direction along the longitudinal axis of the guide member 204 in response to the moving of the wheel 206.

The wheel 206 is connected to the platform 202. The wheel 206 contacts a surface of the tubular member 216 so as to move the platform 202 along and around the tubular member 216 relative to the rotation of the tubular member 216.

As will be described in association with FIG. 11, a tubular member rotation mechanism 224 is provided so as to receive the tubular member 216 and to rotate the tubular member around a longitudinal axis of the tubular member. The tubular member rotation means is supported on the first support structure 220 and on the second support structure 222.

Figure 9:
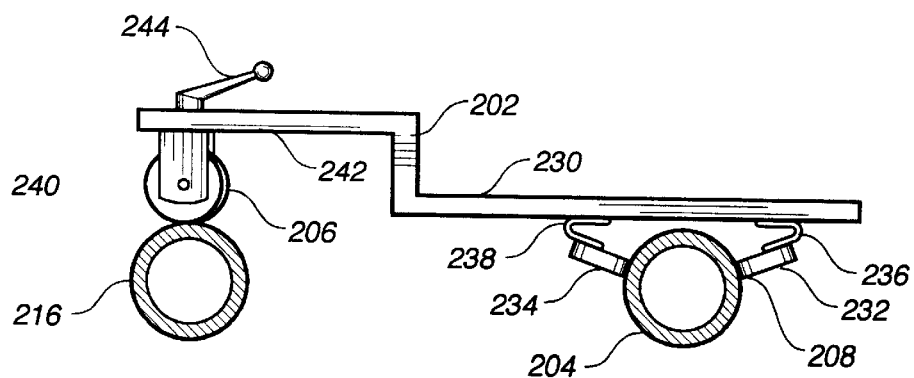
FIG. 9 is a end view showing the configuration of the ultrasonic inspection cart as used in the alternative embodiment of FIG. 8.

FIG. 9 shows the inspection cart 230. Inspection cart 230 includes platform 202 having bearings 208 on one side and inspection wheel 206 on an opposite side. In FIG. 9, it can be seen that the bearings 208 include roller members 232 and 234 that are rotatably attached by brackets 236 and 238, respectively, to the platform 202. The roller members 232 and 234 have a surface in surface-to-surface contact with the guide member 204. In this manner, the roller members 232 and 234 can roll longitudinally along the length of the guide member 204. As shown in FIG. 9, the guide member 204 is a tubular member. However, as stated previously, the guide member 204 can be a solid rod, a square tube, or other longitudinal configuration. The rollers 232 and 234 have an axis about which the wheel rotates. This axis will be in transverse relationship to the longitudinal axis of the guide member 204.

In FIG. 9, it can be seen that the wheel 206 is supported by a support 240 from the underside 242 of the platform 202. The wheel 206 is rotatably mounted to the support 240. The wheel 206 has an outer surface which is in surface-to-surface contact with the exterior surface of the tubular member 216. As the tubular member 216 rotates, the inspection wheel 206 will also rotate. As will be described hereinafter, the wheel 206 has an axis about which the wheel rotates which is angularly offset from the longitudinal axis of the tubular member 216. As such, the rotation of the tubular member 216 will cause the wheel 216 to move along and around the tubular member 216. An adjustment knob 244 is connected to the support 240 so as to allow for the adjustment of the angular offset of the wheel 206 relative to the longitudinal axis of the tubular member 216.

FIG. 10 shows the inspection cart 230 as having platform 202 extending across guide member 204 and tubular member 216. In FIG. 10, it can be seen that a first pair of roller members 232 and a second pair of roller members 234 are positioned on opposite sides of the guide member 204. Each of the roller members 232 and 234 rolls along the exterior surface of the guide member 204 as the inspection cart 230 traverses the length of the tubular member 216. Lines 250 and 252 extend to the inspection unit so as to transmit signals from the inspection wheel 206. It can be seen that the inspection wheel 206 is canted at an angle relative to the longitudinal axis of the tubular member 216. Support 240 serves to retain the wheel 206 at this canted angle. The canting of the angle of the wheel 206 relative to the tubular members 216 causes the inspection cart 230 to move along the length of the guide member 204 and the tubular member 216 as the tubular member 216 rotates.

FIG. 11 is a detailed view showing how the tubular member 216 is rotated. As can be seen, the tubular member 216 is a drill pipe which has a notch 260 formed in a collar 262 at an end of the tubular member 216. A drive wheel 264 is received within the notch 260. Specifically, the notch 260 is received between a pair of drive wheels which serve to rotate the tubular member 216. A motor 266 is provided and is operatively connected to the drive wheel 264 so as to cause the rotational movement of the drill pipe 216.

With reference to FIG. 8, the support structure 220 includes idler rollers of a similar configuration as the drive wheel 264. These idler rollers allow the opposite end of the tubular member 216 to rotate relative to the rotational movement imparted by the drive wheels 264.

FIG. 12 is a diagrammatic illustration of how the guide member support mechanism 218 can cause the guide member 204 to be pivotted at any angle relative to the tubular member 216. In all of the various angular positions of the guide member 204, the inspection wheel 206 will be in surface-to-surface contact with the tubular member 216. As such, it can be seen that the guide member 204 can be rotated in any position so as to allow for the proper inspection of the tubular member 216.

FIG. 13 shows an alternative embodiment of system 300 for the ultrasonic inspection of a tubular member 302. In the embodiment shown in FIG. 13, the tubular member 302 actually serves as the guide member for the system. As can be seen, a platform 304 extends generally around the exterior of the tubular member 302. The ultrasonic inspection wheel 306 is arranged in canted surface-to-surface contact with the tubular member 302. So as to allow the wheel 306 to remain in proper contact with the tubular member 302, a first roller member 308 is positioned in surface-to-surface contact with the tubular member 302 on one side of the wheel 306. Another roller member 310 is positioned in surface-to-surface contact with the tubular member 302 and on an opposite side of the wheel 306. The roller members 308 and 310 serve as the bearings in the system 300 of the present invention. These roller members 308 and 310 are radially offset from the inspection wheel 306. Importantly, a counterbalance 312 is affixed to the platform 304 so as to support the wheel 306 at a desired position on the tubular member 302 as the tubular member 302 rotates. The counterbalance 312 should have sufficient weight so as to properly balance the wheel 306 in its desired location.

A handle 314 is provided on the top of platform 304 so as to allow for the adjusting of the angle of cant of the inspection wheel 306 relative to the tubular member 302. Adjustment handles 316 and 318 are associated with the roller members 308 and 310, respectively.

Figure 14:
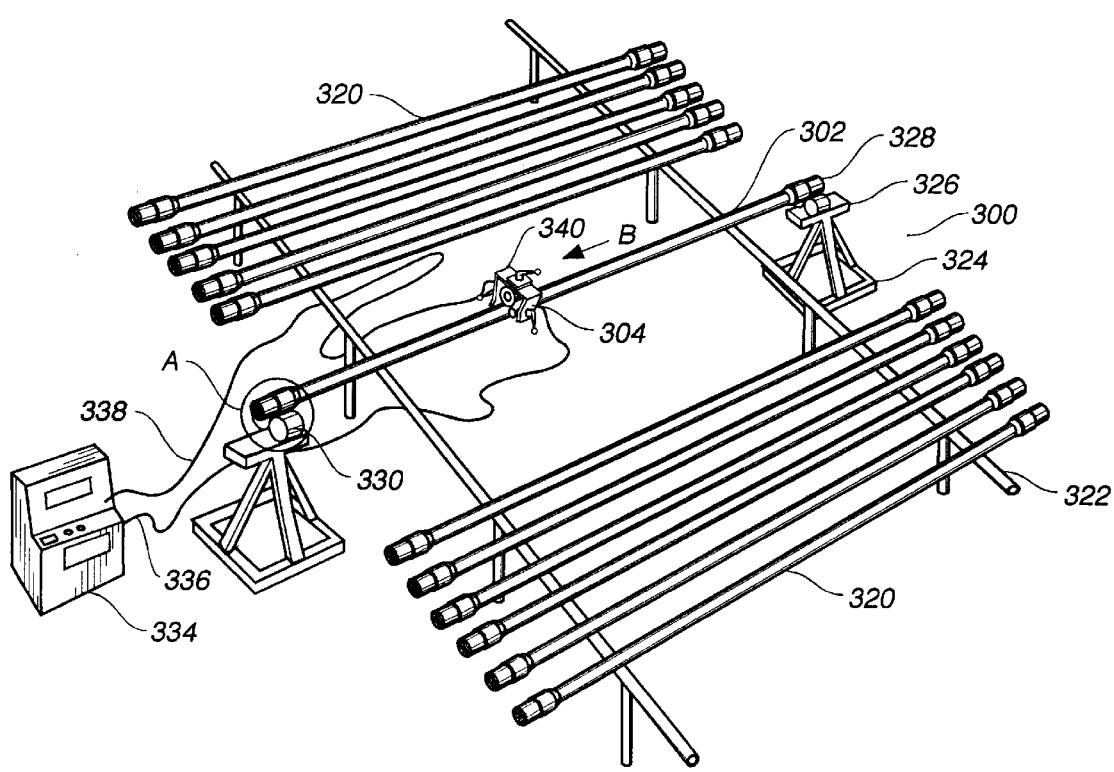
FIG. 14 is a perspective view of the ultrasonic inspection system in accordance with the second alternative embodiment of FIG. 13.

FIG. 14 shows the system 300 as applied to the inspection of drill pipe. In FIG. 14, drill pipe 302 is supported on a pipe rack 322. The drill pipe 302 is supported at one end by a support structure 322 and at the opposite end by a support structure 324. Support structure 322 includes idler rollers 326 so as to allow for the free rotation of the end 328 of drill pipe 302. The support structure 324 includes the drive wheels 330 which serve to impart rotational movement to the drill pipe 302.

An ultrasonic inspection unit 334 is connected by lines 336 and 338 to the inspection cart 340. As such, information passed from the inspection wheel 306 can be transmitted to the inspection unit 334 as the platform 304 traverses the length of the tubular member 302.

As can be seen in FIG. 14, the present invention can, if needed, be adapted so that only a single length of drill pipe can be used so as to guide the inspection unit along the length of the tubular member.

The foregoing disclosure and description of the invention is illustrative and explanatory thereof. Various changes in the details of the illustrated construction may be made within the scope of the appended claims without departing from the true spirit of the invention. The present invention should only be limited by the following claims and their legal equivalents.

I claim:

1. A system for ultrasonic inspection of a tubular member using an ultrasonic inspection unit comprising:

a platform;

a guide member having a longitudinal axis;

a wheel means connected to said platform, said wheel means contacting a surface of the tubular member for moving said platform along and around the tubular member relative to a rotation of the tubular member; and a bearing means connected to said platform at a location spaced from said wheel means, said bearing means contacting said guide member for supporting the platform on the guide member and for allowing the platform to move longitudinally in a direction along said longitudinal axis of said guide member in response to the moving of said wheel means.

2. The system of claim 1, further comprising:

a tubular member rotation means disposed proximate the tubular member for receiving the tubular member and for rotating the tubular member around a longitudinal axis of the tubular member.

3. The system of claim 1, said guide member disposed in a spaced and generally parallel relationship to the tubular member.

4. The system of claim 1, further comprising:

non-destructive inspection means electrically connected to said platform for ultrasonically inspecting the tubular member.

5. The system of claim 4, said wheel means comprising an ultrasonic inspection wheel, said ultrasonic inspection wheel being connected to said non-destruction inspection means.

6. The system of claim 1, said wheel means comprising:

a wheel rotatably mounted on said platform, said wheel having a surface contacting the surface of the tubular member, said wheel having an axis about which said wheel rotates, said axis being angularly offset from a longitudinal axis of the tubular member.

7. The system of claim 1, said guide member being a longitudinal member arranged in spaced parallel relationship to the tubular member, the system further comprising:

a guide member support means connected to said guide member, said guide member support means for positioning said guide member at a desired angle relative to the tubular member.

8. The system of claim 1, said bearing means comprising:

a plurality of roller members rotatably mounted to said platform, each of said plurality of roller members having an axis about which the roller member rotates, said axis being transverse to a longitudinal axis of said guide member.

9. The system of claim 8, said plurality of roller members comprising:

a first pair of roller members in surface-to-surface contact with said guide member on one side of said guide member; and a second pair of roller members in surface-to-surface contact with said guide member on another side of said guide member.

10. The system of claim 1, said guide member being the tubular member.

11. The system of claim 10, said bearing means being radially spaced from said wheel means relative to said guide member.

12. The system of claim 11, said bearing means comprising:

a first roller member in surface-to-surface contact with said guide member on one side of said wheel means; and a second roller member in surface-to-surface contact with said guide member on an opposite side of said wheel means.

13. The system of claim 10, further comprising:

a counterbalance means connected to said platform, said counterbalance means for supporting said wheel means at a desired position on the tubular member as the tubular member rotates.

14. The system of claim 10, said wheel means comprising:

a wheel rotatably mounted on said platform, said wheel having a surface contacting the surface of the tubular member, said wheel having an axis about which said wheel rotates, said axis being angularly offset from a longitudinal axis of the tubular member.

15. The system of claim 2, said tubular member rotation means comprising:

a drive wheel contacting a surface of said tubular member; and a motor means connected to said drive wheel for rotating said drive wheel in a desired direction.

16. The system of claim 15, said tubular member rotation means further comprising:

an idler roller receiving said tubular member at a location along a length of said tubular member, said drive wheel and said idler roller supporting said tubular member a desired distance above a pipe rack.

17. The system of claim 1, said wheel means being pivotally mounted to said platform.

18. The system of claim 17, said wheel means comprising:

a wheel having an axis about which the wheel rotates, said wheel being pivotally mounted to said platform so as to form an adjustable angle of said axis relative to a longitudinal axis of the tubular member.

* * * * *